United States Patent [19]

Aoyagi

[11] Patent Number: 4,465,675
[45] Date of Patent: Aug. 14, 1984

[54] INSECTICIDAL AND FUNGICIDAL 1-ALKYL-5-ALKYLSULFONYL-4-CHLOROPYRAZOLE-3-YL-(THIO)PHOSPHATES AND (THIO)PHOSPHONATES

[75] Inventor: Edward I. Aoyagi, Petaluma, Calif.

[73] Assignee: Chevron Research Company, San Francisco, Calif.

[21] Appl. No.: 453,413

[22] Filed: Dec. 27, 1982

[51] Int. Cl.$^3$ .................. A01N 59/26; C07F 9/65
[52] U.S. Cl. ................................ 424/200; 548/116
[58] Field of Search ................. 548/116; 424/200

[56] References Cited

U.S. PATENT DOCUMENTS 3,843,679  10/1974  Hoffmann et al. ................ 548/116

Primary Examiner—Richard Raymond
Attorney, Agent, or Firm—S. R. LePaglia; T. G. DeJonghe; S. L. Biggs

[57] ABSTRACT

Compounds of the formula:

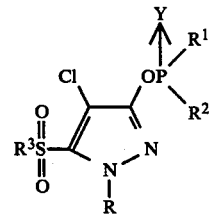

wherein R is lower alkyl; $R^1$ is lower alkoxy or lower alkylthio; $R^2$ is lower alkyl or lower alkoxy; $R^3$ is lower alkyl; and Y is sulfur or oxygen, possess fungicidal and insecticidal activity.

27 Claims, No Drawings

INSECTICIDAL AND FUNGICIDAL 1-ALKYL-5-ALKYLSULFONYL-4-CHLOROPYRAZOLE-3-YL-(THIO)PHOSPHATES AND (THIO)PHOSPHONATES

BACKGROUND OF THE INVENTION

This invention is drawn to novel compounds which are effective as insecticides and fungicides.

With the world more dependent for food on an ever-decreasing amount of cultivated land, it is necessary to develop fungicides and insecticides which protect crops from pesticidal destruction.

United Kingdom Patent Application GB No. 2,013,182A discloses the use of 1- or 2-alkyl-5-substituted pyrazole-3-yl-(thio)phosphates and (thio)phosphonates as insecticides, acaricides and nematocides.

U.S. Pat. No. 3,952,098 discloses pyrazolo-(thiono)-phosphoric acid esters as insecticidal.

U.K. Pat. No. 1,535,498 and U.S. Pat. No. 4,163,052 disclose pyrazolyl-(thio)phosphates, (thio)phosphonates and phosphoramides useful as insecticides, acaricides and nematocides.

SUMMARY OF THE INVENTION

The 1-alkyl-5-alkylsulfonyl-4-chloropyrazole-3-yl-(thio)phosphates and (thio)phosphonates of this invention are represented by the formula:

$$\text{I}$$

wherein R is lower alkyl; $R^1$ is lower alkoxy or lower alkylthio; $R^2$ is lower alkyl or lower alkoxy; $R^3$ is lower alkyl; and Y is sulfur or oxygen.

Among other factors, the present invention is based on my findings that the compounds of this invention possess good insecticidal activity, especially against Cabbage Looper. Some of the compounds of this invention also surprisingly possess fungicidal activity, particularly against Bean Powdery Mildew.

In part due to their superior insecticidal and fungicidal activity, preferred R lower alkyl groups include, for instance, methyl, ethyl, isopropyl, n-hexyl, and the like. Particularly preferred R groups are ethyl and methyl. Most preferably, R is methyl.

Preferred $R^1$ groups include methoxy and ethoxy. Preferred $R^2$ groups include methyl and ethyl.

Preferably Y is sulfur.

DEFINITIONS

As used herein, the following terms have the following meanings, unless expressly stated to the contrary.

The term "alkyl" refers to both straight- and branched-chain alkyl groups.

The term "lower alkyl" refers to both straight- and branched-chain alkyl groups having a total from 1 to 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "alkoxy" refers to the group R'O— wherein R' is alkyl.

The term "lower alkoxy" refers to alkoxy groups having from 1 to 6 carbon atoms and includes, for example, methoxy, ethoxy, t-butoxy, hexoxy, and the like.

The term "alkylthio" refers to the group R'S— wherein R' is alkyl.

The term "lower alkylthio" refers to alkylthio groups having from 1 to 6 carbon atoms; examples include methylthio, ethylthio, isopropylthio, and the like.

The term "sulfonyl" refers to the —$SO_2$— group.

The term "alkylsulfonyl" refers to the $R'SO_2$— group where R' is alkyl.

The term "pyrazole" refers to the group. The conventional numbering system for this group is shown below.

DETAILED DESCRIPTION OF THE INVENTION

The compounds of this invention wherein $R^2$ is lower alkoxy are conveniently prepared according to the following scheme:

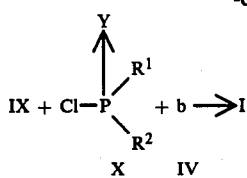

(4)

wherein R, $R^1$, $R^2$, $R^3$, and Y are as defined in conjunction with formula above; b is an organic or inorganic base; and $R^5$ is lower alkyl.

Reaction (1) is conducted by adding an essentially equimolar amount of III to II. An essentially equimolar amount of a base, b, is added to the reaction to scavenge the acid generated. Either organic or inorganic bases may be employed. Preferably, an organic base such as trialkylamine (e.g., triethylamine), pyridine and the like is employed. The reaction is conducted in the liquid phase employing an inert organic solvent such as methanol, ethanol, tetrahydrofuran, and the like. The reaction is exothermic and cooling may be necessary. The reaction is generally conducted from 0°–50° C., although preferably at from 20°–35° C. Reaction pressure is not critical and for convenience, reaction pressure is atmospheric. The reaction is generally complete within 1–24 hours. The product, VI, is isolated by conventional procedures such as extraction, filtration, chromatography, distillation, or alternatively, used in Reaction (2) without purification and/or isolation.

Reaction (2) is conducted by adding an essentially equimolar amount of an alkyl hydrazine, VI, to V using an equimolar amount of a base, b, to yield the pyrazole, VII. The reaction is conducted in the liquid phase using an inert organic solvent such as benzene, toluene, tetrahydrofuran, and the like. A base is employed to scavenge the acid generated in the reaction. Either an organic or inorganic base may be used. Suitable organic bases include, for instance, trialkylamines, pyridine, and the like. Suitable inorganic bases include sodium bicarbonate, potassium carbonate, sodium carbonate, and the like. Preferably, an inorganic base such as potassium carbonate, sodium carbonate, potassium bicarbonate, and the like, is employed. The reaction is exothermic and cooling may be necessary during addition of the reagents. The reaction is generally conducted from 0°–110° C. and is generally complete within 1–24 hours. Reaction pressure is not critical and for convenience, atmospheric pressure is used. The resulting pyrazole, VII, is isolated by conventional procedures such as extraction, filtration, chromatography, crystallization, or alternatively used in Reaction (3) without purification and/or isolation.

The pyrazole sulfide, VII, is converted to the corresponding sulfone, IX, by reacting VII with 2 equivalents of an oxidizing agent such as m-chloroperoxybenzoic acid (MCPBA) as shown in Reaction (3). The reaction is conducted in the liquid phase using an inert organic solvent such as chloroform, dichloromethane, and the like. Alternatively, hydrogen peroxide may be used as the oxidizing agent in a liquid phase of acetic acid. The reaction is generally conducted at a temperature of 0°–100° C. and is generally complete within 1–72 hours. Reaction pressure is not critical and for convenience, the reaction pressure is generally atmospheric. The sulfone, IX, is isolated and purified by conventional procedures such as extraction, filtration, chromatography, crystallization, or alternatively used in Reaction (4) without purification and/or isolation.

Alternatively, when the MCPBA was used as the oxidizing agent, the sulfone, IX, may be purified in the following manner. Upon reaction completion, the solvent is removed by stripping. The crude product is dissolved in either methanol or ethanol containing approximately 1% of a strong acid such as sulfuric acid, hydrochloric acid, and the like. The system is heated to reflux for 1–24 hours. Afterwards, a large excess of an organic solvent, such as diethyl ether, ethyl acetate, toluene, and the like, is added. The product is then extracted with a basic aqueous solution. Upon acidification of this solution, the product precipitates out.

Reaction (4) is conducted by adding essentially equimolar amounts of either dialkoxychlorothiophosphate or dialkoxychlorophosphate, X, to IX. The reaction is conducted in the liquid phase using an organic solvent such as methyl ethyl ketone, acetone, dimethoxyethane, chloroform, and the like. Between 1 and 2 equivalents of an organic or inorganic base is added to the system to scavenge the acid generated by the reaction. Preferably, an inorganic base such as potassium carbonate, potassium bicarbonate, and the like, is used. Reaction pressure is not critical and for convenience, the reaction pressure is generally atmospheric. The reaction is heated at reflux and is generally complete within 1–24 hours. The product, I, is isolated by conventional procedures such as extraction, filtration, chromatography, and the like.

The compounds of this invention where $R^2$ is lower alkyl are conveniently prepared by treating intermediate IX [prepared according to Reactions (1) and (3) above] according to the following synthetic scheme:

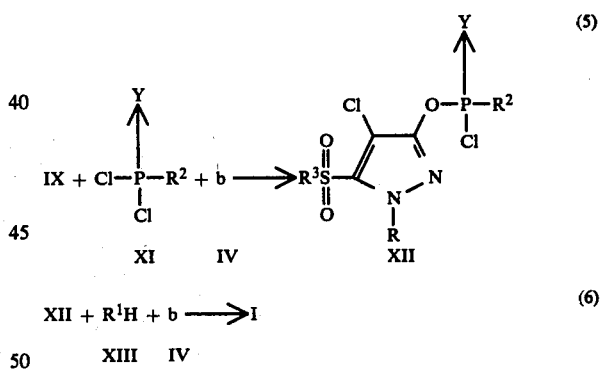

(5)

XII + $R^1$H + b ⟶ I (6)

XIII IV wherein R, $R^1$, $R^2$, $R^3$, Y and b are as previously defined.

Reaction (5) is conducted by adding essentially equimolar amounts of XI and IV to IX. Suitable bases, IV, include organic and inorganic bases such as triethylamine, pyridine, potassium carbonate, and the like. The reaction is conducted in the liquid phase using an organic solvent such as methyl ethyl ketone, acetone, dimethoxyethane, chloroform, and the like. Reaction pressure is not critical and, for convenience, the reaction is carried out at ambient pressure. The reaction is generally conducted at a temperature of about 0° C. to about 50° C., and for convenience may be carried out in the temperature range of about 20° C. to about 35° C. The reaction generally is complete within about 1 to about 24 hours. The product is isolated by conventional procedures such as extraction, filtration, chromatography, or alternatively used in Reaction (6) without purification and/or isolation.

Reaction (6) is conducted by adding approximately equimolar amounts of XIII and IV to XII. Suitable bases IV include organic and inorganic bases such as triethylamine, pyridine, potassium carbonate, and the like. The reaction is conducted in the liquid phase using an organic solvent such as methyl ethyl ketone, acetone, dimethoxyethane, chloroform, and the like. Reaction pressure is not critical and, for convenience, the reaction is carried out at ambient pressure. The reaction is generally conducted at a temperature of about 20° C. to about 100° C.; and, for convenience, it may be conducted at ambient temperature. The product, I, is isolated by conventional procedures such as extraction, filtration, chromatography, and the like.

UTILITY

The compounds of this invention are useful for controlling insects, particularly such insects as Cabbage Looper (*Trichoplusia ni*). However, some insecticidal compounds of this invention may be more insecticidally active than others against particular pests.

Like most insecticides, they are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hosts susceptible to insect attack. They may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from 5–80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing or emulsifying agents used in insecticidal formulations include, for example, the alkyl and alkylaryl sulfonates and sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1–15% by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersants, and may consist entirely of the toxicant with a liquid or solid emulsifying agent, or may also contain a liquid carrier such as xylene, heavy aromatic naphthas, isophorone, and other nonvolatile organic solvents. For application, these concentrates are dispersed in water or other liquid carriers, and are normally applied as a spray to the area to be treated.

Other useful formulations for insecticidal applications include simple solutions of the active ingredient in a dispersant in which it is completely soluble at the desired concentration such as acetone, alkylated naphthalenes, xylene, or other organic solvents. Granular formulations, wherein the toxicant is carried on relatively coarse particles, are of particular utility for aerial distribution or for penetration of cover-crop canopy. Baits, prepared by mixing solid or liquid concentrates of the toxicant with a suitable food such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier such as the Freons, may also be used. All of these techniques for formulating and applying the active ingredient are well known in the art.

The percentages by weight of the toxicant may vary according to the manner in which the composition is to be applied and the particular type of formulation, but in general comprise 0.1–95% of the toxicant by weight of the insecticidal composition.

The insecticidal compositions may be formulated and applied with other active ingredients, including nematocides, insecticides, fungicides, bactericides, plant-growth regulators, fertilizers, etc. In applying the chemical, an effective amount and concentration of the toxicant of this invention is, of course, employed.

The terms "insecticide" and "insect" as used herein refer to their broad and commonly understood usage rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs, such as spiders, mites, ticks, centipedes, worms, and the like.

The compounds of this invention are also useful for controlling fungi. Additionally, some of the compounds of this invention are particularly effective in controlling powdery mildew caused by organisms such as *Erysiphe polygoni*.

However, some fungicidal compounds of the invention may be more fungicidally active than others against particular fungi. Table II lists a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, powdery dusts, wettable powders, emulsifiable concentrates, solutions, or as any several other known types of formulations, depending on the desired mode of application.

Wettable powders are in the form of finely divided particles which disperse readily in water or other dispersants. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, organic diluents. Typical wetting, dispersing or emulsifying agents include, for example, the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1–15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersants, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carriers, and are normally applied as a spray to the area to be treated.

Other useful formulations for fungicidal applications include simple solutions of the active fungicide in a dispersant in which it is completely soluble at the desired concentration such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5–95% of the toxicant by weight of the fungicidal composition.

The fungicidal composition may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperatures and temperature ranges refer to the Centigrade system and the term "ambient" or "room temperature" refers to about 20°–25° C. The term "percent" refers to weight percent and the term "mol" or "mols" refers to gram mols. The term "equivalent" refers to a quantity of reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly, isomer mixtures are obtained as products.

EXAMPLES

Example 1

Preparation of Methyl-2,3-dichloro-3-ethylthioacrylate

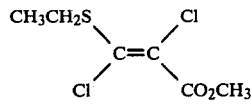

A solution of 270 gms of ethanethiol and 580 ml (419 gms) of triethylamine in 1 liter of methanol was slowly added to 795 gms methyl trichloroacrylate. The addition was exothermic and cooling was required. After addition, the reaction mixture was stirred at room temperature for 18 hours. At this time, an additional 20 gms of ethanethiol was added and the system stirred for an additional 2 hours. The solvent and excess ethanethiol were removed under reduced pressure. The resulting oil was dissolved in methylene chloride. The organic solution was washed with water, dried over magnesium sulfate and filtered. The methylene chloride was removed by stripping to give 860 gms of a brown liquid. The crude product was purified by vacuum distillation to give 600 gms of the methyl-2,3-dichloro-3-ethylthioacrylate (collected at 135°–145° C. at 20 mm Hg).

Example 2

Preparation of 4-chloro-3-hydroxy-1-methyl-5-ethylthiopyrazole

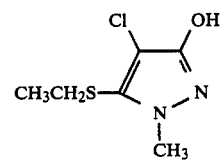

To the solution of methyl-2,3-dichloro-3-ethylthioacrylate (the product of Example 1), 577.1 gms, in 1.5 liters of toluene, was added 370 gms of potassium carbonate followed by slow addition of 123.6 gms of methylhydrazine. The addition was exothermic and cooling of the system was occasionally necessary. When addition of the methylhydrazine was completed, the reaction mixture was allowed to come to room temperature and stirred there for 24 hours. The reaction mixture was then refluxed for an additional 24 hours. The solution was then filtered and the precipitate collected. The toluene filtrate gave ca. 70 gms of the product. The major portion of the product was present in the precipitate as a potassium salt and isolated as follows: The precipitate was added to 2 liters of 10% HCl solution and the product was extracted with methylene chloride. The methylene chloride was concentrated to approximately 500 ml by stripping whereupon the 4-chloro-3-hydroxy-1-methyl-5-ethylthiopyrazole crystallized from solution. The total yield of the final product was 334 gms.

Example 3

Preparation of Methyl-2,3-dichloro-3-methylthioacrylate

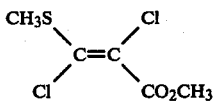

A solution of 4.85 gms (92 mmols) of methanethiol and 9.3 gms (92 mmols) of triethylamine in methanol was slowly added to 17.6 gms (92 mmols) trichloroacrylate with cooling. After addition, the reaction system was stirred at room temperature for about 20 hours. The solvent and excess methanethiol were removed under reduced pressure. Ether was added to the residue (crude product) and the precipitated solvents filtered. The ether was removed under reduced pressure to give an oil. The oil was distilled to give 11.6 gms of a low melting point solid (boiling point 125°–150° C. at approximately 50 mm Hg; melting point 27°–30° C.).

Example 4

Preparation of 4-Chloro-3-hydroxy-1-methyl-5-methylthiopyrazole

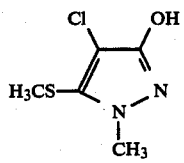

To a stirred solution of 11.6 gms (58 mmols) methyl-2,3-dichloro-3-methylthioacrylate (the product of Example 3) and 8.0 gms (58 mmols) potassium carbonate in 150 mls toluene, 2.1 gms (58 mmols) methylhydrazine were added dropwise. The reaction mixture was heated at 80° C. for about 8 hours. Then an additional 0.5 gm methylhydrazine was added; the resulting mixture was heated to reflux and refluxed for 2 hours. The reaction mixture was cooled and then filtered to remove solids. Stripping of the filtrate, followed by chromatography of the residue on silica gel eluting with ethyl acetate, gave 2.8 gms of the product as a solid with a melting point of 163°–165° C.

Example 5

Preparation of 4-Chloro-3-hydroxy-1-methyl-5-methylsulfonyl-pyrazole

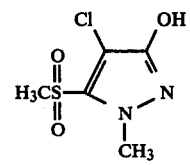

To a solution of 11.4 gms (64 mmols) 4-chloro-3-hydroxy-1-methyl-5-methylthiopyrazole (the product of Example 4) in 200 mls chloroform, 29.4 gms (145 mmols) of 85% m-chloro-peroxybenzoic acid (MCPBA) were added in small portions. The reaction mixture was stirred about 24 hours. Then the reaction mixture was filtered to remove solids. Stripping of the filtrate gave a residue containing the product and (excess) MCPBA and some m-chlorobenzoic acid.

Removal of the acids: The residue was dissolved in methanol. A few drops of sulfuric acid (concentrated) were added to the mixture and the resulting solution was refluxed for about 24 hours. At that time, the reaction mixture was cooled and the solvent partially stripped. The mixture was then diluted with ether. The ether mixture was washed with a cold saturated sodium bicarbonate solution. The sodium bicarbonate solution phase was separated and then acidified to precipitate the product, yielding 10 gms of a solid with a melting point of 249°–251° C.

Example 6

Preparation of O,O-diethyl-O-(4-chloro-1-methyl-5-methylsulfonyl-pyrazole-3-yl)-thiophosphate

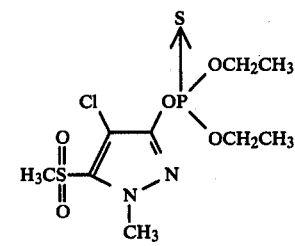

A mixture of 7.0 gms (33 mmols) 4-chloro-3-hydroxy-1-methyl-5-methylsulfonylpyrazole, 6.6 gms (35 mmols) diethylchlorothiophosphate and 4.6 gms (33 mmols) potassium carbonate in 50 mls methyl ethyl ketone was refluxed for 20 minutes. The reaction mixture was cooled. Stripping of the solvent gave a residue which was taken up in water and extracted with ether. The ether phase was dried over magnesium sulfate and stripped to give 8.6 gms of the product, O,O-diethyl-O-(4-chloro-1-methyl-5-methylsulfonylpyrazole-3-yl)-thiophosphate.

Example 7

Preparation of
Ethyl-O-ethyl-O-(4-chloro-1-methyl-5-ethylsulfonyl-pyrazole-3-yl)-thiophosphonate

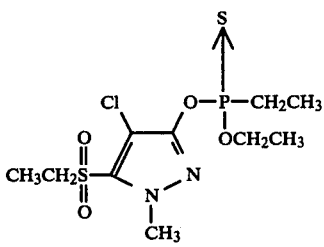

(a) To a stirred solution of 4.1 gms (18.2 mmols) 4-chloro-3-hydroxy-1-methyl-5-ethylsulfonylpyrazole and 3.12 gms (19.1 mmols) ethylphosphonothioic dichloride in 100 mls methylene chloride, 1.93 gms (19.1 mmols) triethylamine were added. The reaction mixture was stirred overnight at room temperature to give the ethyl-O-(4-chloro-1-methyl-5-ethylsulfonylpyrazole-3-yl)-thiophosphinyl chloride intermediate which was used in situ.

(b) To the mixture from Step (a), 2 gms (36.4 mmols) ethanol and 2.7 gms triethylamine were added and the resulting mixture was stirred at room temperature for several days. The reaction mixture stripping of the solvent, followed by chromatography on silica gel eluting with methylene chloride, gave 3.2 gms of product, an oil.

Compounds made in accordance with Examples 1 to 7 are shown in Table I.

In addition, by following the procedures described in Examples 1 to 7 using the appropriate starting materials, the following compounds are made:

O,O-diethyl-O-(4-chloro-1-methyl-5-methylsulfonyl-pyrazole-3-yl)-phosphate;
O,O-dimethyl-O-(4-chloro-1methyl-5-ethylsulfonyl-pyrazole-3-yl)-phosphate;
O,O-diisopropyl-O-(4-chloro-1-methyl-5-ethylsulfonyl-pyrazole-3-yl)-phosphate;
O,O-di-n-hexyl-O-(4-chloro-1-methyl-5-ethylsulfonyl-pyrazole)-phosphate;
O,O-diisopropyl-O-(4-chloro-1-ethyl-5-methylsulfonyl-pyrazole-3-yl)-phosphate;
O,O-diethyl-O-(4-chloro-1-methyl-5-ethylsulfonyl-pyrazole-3-yl)-phosphate;
O,O-diethyl-O-(4-chloro-1-ethyl-5-n-hexylsulfonyl-pyrazole-3-yl)-phosphate;
O,O-dimethyl-O-(4-chloro-1-methyl-5-methylsulfonyl-pyrazole-3-yl)-phosphate;
O,O-dimethyl-O-(4-chloro-1-n-propyl-5-isopropylsulfonylpyrazole-3-yl)-phosphate;
O,O-diethyl-O-(4-chloro-1-n-propyl-5-isopropylsulfonylpyrazole-3-yl)-phosphate;
O,O-diethyl-O-(4-chloro-1-n-hexyl-5-n-propylsulfonyl-pyrazole-3-yl)-phosphate;
O,O-dimethyl-O-(4-chloro-1-n-hexyl-5-n-propylsulfonylpyrazole-3-yl)-phosphate;
O,S-dimethyl-O-(4-chloro-1-methyl-5-ethylsulfonyl-pyrazole-3-yl)-thiophosphate;
O,S-diethyl-O-(4-chloro-1-methyl-5-methylsulfonyl-pyrazole-3-yl)-thiophosphate;
O-ethyl,S-methyl-O-(4-chloro-1-methyl-5-methylsulfonylpyrazole-3-yl)-thiophosphate;
O-ethyl,S-isopropyl-O-(4-chloro-1-methyl-5-methylsulfonylpyrazole-3-yl)-thiophosphate;
O-methyl,S-ethyl-O-(4-chloro-1-n-propyl-5-n-hexylsulfonylpyrazole-3-yl)-thiophosphate;
O,O-dimethyl-O-(4-chloro-1-methyl-5-ethylsulfonyl-pyrazole-3-yl)-thiophosphate;
O,O-diisopropyl-O-(4-chloro-1-methyl-5-ethylsulfonyl-pyrazole-3-yl)-thiophosphate;
O,O-di-n-hexyl-O-(4-chloro-1-methyl-5-ethylsulfonyl-pyrazole-3-yl)-thiophosphate;
O,O-di-n-propyl-O-(4-chloro-1-methyl-5-methylsulfonyl-pyrazole-3-yl)-thiophosphate;
O,O-dimethyl-O-(4-chloro-1-methyl-5-ethylsulfonyl-pyrazole-3-yl)-thiophosphate;
O,O-dimethyl-O-(4-chloro-1-methyl-5-methylsulfonyl-pyrazole-3-yl)-thiophosphate;
O,O-diethyl-O-(4-chloro-1-ethyl-5-n-hexylsulfonyl-pyrazole-3-yl)-thiophosphate;
O,O-diethyl-O-(4-chloro-1-n-propyl-5-isopropylsulfonylpyrazole-3-yl)-thiophosphate;
O,O-diethyl-O-(4-chloro-1-n-hexyl-5-n-propylsulfonylpyrazole-3-yl)-thiophosphate;
O-ethyl,O-methyl-O-(4-chloro-1-n-hexyl-5-n-propylsulfonylpyrazole-3-yl)-thiophosphonate;
O-ethyl,O-methyl-O-(4-chloro-1-methyl-5-methylsulfonylpyrazole-3-yl)-thiophosphate;
O-methyl,S-methyl-O-(4-chloro-1-methyl-5-ethylsulfonylpyraozle-3-yl)-dithiophosphate;
O-ethyl,S-ethyl-O-(4-chloro-1-methyl-5-methylsulfonylpyrazole-3-yl)-dithiophosphate;
O-ethyl,S-methyl-O-(4-chloro-1-methyl-5-methylsulfonylpyrazole-3-yl)-dithiophosphate;
O-ethyl,S-isopropyl-O-(4-chloro-1-methyl-5-methylsulfonylpyrazole-3-yl)-dithiophosphate;
O-methyl,S-ethyl-O-(4-chloro-1-n-propyl-5-n-hexylsulfonylpyrazole-3-yl)-dithiophosphate;
Ethyl-O-ethyl-O-(4-chloro-1-methyl-5-methylsulfonylpyrazole-3-yl)-phosphonate;
Methyl-O-methyl-O-(4-chloro-1-methyl-5-ethylsulfonylpyrazole-3-yl-phosphonate;
Isopropyl-O-isopropyl-O-(4-chloro-1-methyl-5-ethylsulfonylpyrazole-3-yl)-phosphonate;
N-hexyl-O-n-hexyl-O-(4-chloro-1-methyl-5-ethylsulfonylpyrazole-3-yl)-phosphonate;
Ethyl-O-isopropyl-O-(4-chloro-1-ethyl-5-methylsulfonylpyrazole-3-yl)-phosphonate;
Methyl-O-ethyl-O-(4-chloro-1-methyl-5-ethylsulfonylpyrazole-3-yl)-phosphonate;
Ethyl-O-methyl-O-(4-chloro-1-ethyl-5-n-hexylsulfonylpyrazole-3-yl)-phosphonate;
Methyl-O-methyl-O-(4-chloro-1-methyl-5-methylsulfonylpyrazole-3-yl)-phosphonate;
Methyl-O-methyl-O-(4-chloro-1-n-propyl-5-isopropylsulfonylpyrazole-3-yl)-phosphonate;
Ethyl-O-ethyl-O-(4-chloro-1-n-propyl-5-isopropylsulfonylpyrazole-3-yl)-phosphonate;
Ethyl-O-ethyl-O-(4-chloro-1-n-hexyl-5-n-propylsulfonylpyrazole-3-yl)-phosphonate;
Methyl-O-methyl-O-(4-chloro-1-n-hexyl-5-n-propylsulfonylpyrazole-3-yl)-phosphonate;
Methyl-S-methyl-O-(4-chloro-1-methyl-5-ethylsulfonylpyrazole-3-yl)-thiophosphonate;
Ethyl-S-ethyl-O-(4-chloro-1-methyl-5-methylsulfonylpyrazole-3-yl)-thiophosphonate;
Ethyl-S-methyl-O-(4-chloro-1-methyl-5-methylsulfonylpyrazole-3-yl)-thiophosphonate;
Ethyl-S-isopropyl-O-(4-chloro-1-methyl-5-methylsulfonylpyrazole-3-yl)-thiophosphonate;

Methyl-S-ethyl-O-(4-chloro-1-n-propyl-5-n-hexylsulfonylpyrazole-3-yl)-thiophosphonate;
Methyl-O-methyl-O-(4-chloro-1-methyl-5-ethylsulfonyl-3-yl)-thiophosphonate;
Isopropyl,O-isopropyl-O-(4-chloro-1-methyl-5-ethylsulfonylpyrazole-3-yl)-thiophosphonate;
N-hexyl-O-n-hexyl-O-(4-chloro-1-methyl-5-ethylsulfonylpyrazole-3-yl)-thiophosphonate;
N-propyl-O-n-propyl-O-(4-chloro-1-methyl-5-methylsulfonylpyrazole-3-yl)-thiophosphonate;
Methyl-O-methyl-O-(4-chloro-1-methyl-5-ethylsulfonylpyrazole-3-yl)-thiophosphonate;
Methyl-O-methyl-O-(4-chloro-1-methyl-5-methylsulfonylpyrazole-3-yl)-thiophosphonate;
Methyl-O-isopropyl-O-(4-chloro-1-methyl-5-methylsulfonylpyrazole-3-yl)-thiophosphonate;
Ethyl-O-ethyl-O-(4-chloro-1-ethyl-5-n-hexylsulfonylpyrazole-3-yl)-thiophosphonate;
Ethyl-O-ethyl-O-(4-chloro-1-n-propyl-5-isopropylsulfonylpyrazole-3-yl)-thiophosphonate;
Ethyl-O-ethyl-O-(4-chloro-1-n-hexyl-5-n-propylsulfonylpyrazole-3-yl)-thiophosphonate;
Ethyl-O-methyl-O-(4-chloro-1-n-hexyl-5-n-propylsulfonylpyrazole-3-yl)-thiophosphonate;
Ethyl-O-methyl-O-(4-chloro-1-methyl-5-methylsulfonylpyrazole-3-yl)-thiophosphonate;
Methyl-O-ethyl-O-(4-chloro-1-methyl-5-methylsulfonylpyrazole-3-yl)-thiophosphonate;
Methyl-O-ethyl-O-(4-chloro-1-methyl-5-ethylsulfonylpyrazole-3-yl)-thiophosphonate;
Ethyl-O-methyl-O-(4-chloro-1-methyl-5-ethylsulfonylpyrazole-3-yl)-thiophosphonate;
Methyl-S-methyl-O-(4-chloro-1-methyl-5-ethylsulfonylpyrazole-3-yl)-dithiophosphonate;
Ethyl-S-ethyl-O-(4-chloro-1-methyl-5-methylsulfonylpyrazole-3-yl)-dithiophosphonate;
Ethyl-S-methyl-O-(4-chloro-1-methyl-5-methylsulfonylpyrazole-3-yl)-dithiophosphonate;
Ethyl-S-isopropyl-O-(4-chloro-1-methyl-5-methylsulfonylpyrazole-3-yl)-dithiophosphonate;
Methyl-S-ethyl-O-(4-chloro-1-n-propyl-5-n-hexylsulfonylpyrazole-3-yl)-dithiophosphonate; and
Methyl-S-isopropyl-O-(4-chloro-1-methyl-5-methylsulfonylpyrazole-3-yl)-dithiophosphonate.

EXAMPLE A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72°-80° F.; relative humidity was maintained at 40-60%. The percent disease control provided by a given test compound was based on the percent disease reduction relative to the untreated check plants. The results are tabulated in Table II.

EXAMPLE B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66°-68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE C

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66°-68° F. in 100% relative humidity for an extended period of time (approximately 48 hours). Following the incubation, the plants were allowed to dry and then were maintained in a greenhouse for approximately 14 days. The percent disease control provided by a given candidate toxicant was based on the percent disease reduction relative to untreated check plants. The results are reported in Table II.

EXAMPLE D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in an environmental chamber and incubated at 66°-68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

EXAMPLE E

Grape Downy Mildew

The compounds of the invention were tested for the control of the Grape Downy Mildew organism *Plasmopara viticola*. Detached leaves, between 7 and 85 mm in diameter, 7-week-old *Vitis vinifera* cultivar Emperor grape seedlings were used as hosts. The leaves were sprayed with a 250-ppm solution of the test compound in acetone. The sprayed leaves were dried, inoculated with a spore suspension of the organism, placed in a humid environmental chamber and incubated at 66°-68° F. and about 100% relative humidity. After incubation for 2 days, the plants were then held in a greenhouse 7-9 days; then the amount of disease control was determined. The percent disease control provided by a given test compound was based on the percent disease reduction relative to untreated check plants. The results are tabulated in Table II.

EXAMPLE F

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68°–70° F. The plants were then removed from the chamber, allowed to dry, and then maintained in a greenhouse at 60–80% relative humidity. The rate of infection on the leaves was made after about 14 days. The percent disease control provided by a given test compound was based on the percent disease reduction relative to untreated check plants. The results are reported in Table II.

EXAMPLE G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated 1 day later with the organism in an environmental chamber. After inoculation, the plants were kept in an environmental chamber for about 48 hours under conditions of about 72°–75° F. and about 100% relative humidity. Following the incubation period, the plants were placed in a greenhouse with a temperature of about 72° F. and maintained with bottom watering for about 12–16 days. The percent disease control provided by a given test compound is based on a comparison of the percentage disease relative to the percent disease development on the untreated check plants.

$$\% \text{ Control} = 100 \times \left( \frac{\% \text{ disease in treated plants}}{\% \text{ disease in check}} \right)$$

The results are tabulated in Table II.

EXAMPLE H

Aphid Control

The compounds of the invention were tested for their insecticidal activity against Cotton Aphids (*Aphis gossypii* Glover). An acetone solution of the candidate toxicant containing a small amount of nonionic emulsifier was diluted with water to 40 ppm. Cucumber leaves infested with the Cotton Aphids were dipped in the toxicant solution. Mortality readings were taken after 24 hours. The results are tabulated in Table III in terms of percent control.

EXAMPLE I

Aphids Systemic Evaluation

This procedure is used to assess the ability of a candidate insecticide to be absorbed through the plant root system and translocate to the foliage.

Two cucumber plants planted in a 4-inch fiber pot with a soil surface area of 80 cm$^2$ are used. Forty ml of an 80-ppm solution of the candidate insecticide is poured around the plants in each pot. (This corresponds to 40 γ/cm$^2$ of actual toxicant.) The plants are maintained throughout in a greenhouse at 75°–85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table III in terms of percent control.

EXAMPLE J

Mite Adult

Two-spotted Mite (*Tetranychus urticae*): An acetone solution of the candidate toxicant containing a small amount of nonionic emulsifier was diluted with water to 40 ppm. Lima bean leaves which were infested with mites were dipped in the toxicant solution. Mortality readings were taken after 24 hours. The results are tabulated in Table III in terms of percent control.

EXAMPLE K

Mite Egg Control

Compounds of this invention were tested for their ovicidal activity against eggs of the two-spotted spider mite (*Tetranychus urticae*). An acetone solution of the test toxicant containing a small amount of nonionic emulsifier was diluted with water to give a concentration of 40 ppm. Two days before testing, 2-week-old lima bean plants were infested with spider mites. Two days after infestation, leaves from the infested plants were dipped in the toxicant solution, placed in a petri dish with filter paper and allowed to dry in the open dish at room temperature. The treated leaves were then held in covered dishes at about 31° C. to 33° C. for seven days. On the eighth day, egg mortality readings were taken. The results, expressed as percent control, are tabulated in Table III.

EXAMPLE L

Housefly

Housefly (*Musca domestica L.*): A 500-ppm acetone solution of the candidate toxicant was placed in a microsprayer (atomizer). A random mixture of anesthetized male and female flies were placed in a container and 55 mg of the above-described acetone solution was sprayed on them. A lid was placed on the container. A mortality reading was made after 24 hours. The results are tabulated in Table III in terms of percent control.

EXAMPLE M

American Cockroach

American Cockroach (*Periplaneta americana L.*): A 500-ppm acetone solution of the candidate toxicant was placed in a microsprayer (atomizer). A random mixture of anesthetized male and female roaches was placed in a container and 55 mg of the above-described acetone solution was sprayed on them. A lid was placed on the container. A mortality reading was made after 24 hours. The results are tabulated in Table III in terms of percent control.

EXAMPLE N

Alfalfa Weevil

Alfalfa Weevil (*H. brunneipennis Boheman*): A 500-ppm acetone solution of the candidate toxicant was placed in a microsprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table III in terms of percent control.

EXAMPLE O

Cabbage Looper Control

The compounds of the invention were tested for their insecticidal activity against Cabbage Looper (*Trichoplusia ni*). An acetone solution of the candidate toxicant containing a small amount of nonionic emulsifier was diluted with water to 500 ppm. Excised cucumber leaves were dipped in the toxicant solution and allowed to dry. They were then infested with Cabbage Looper larvae. Mortality readings were taken after 24 hours. The results are tabulated in Table III in terms of percent control.

EXAMPLE P

Rootworm Control

The compounds of the invention were tested for control of Corn Rootworm (*Diabrotica larvae*). A batch of 20–30 two-day-old Diabrotica eggs was placed on the bottom of a 237-cc clear plastic cup. These eggs were then covered with about 45 cc of soil containing 15 ppm of the test compound. The soil is watered with 15 cc of water. The corn seeds, presoaked for 2 hours, were evenly distributed on the soil surface. Then an additional 45 cc of the same treated soil was added to cover the seeds, and this soil was watered with an additional 15 cc of water. The test cup was kept at 70° C. with occasional light watering just to keep the soil damp.

After 14–16 days, the test unit was examined under a dissecting scope by observing the corn roots and larvae through the cup's clear plastic walls. Control of newly hatched larvae was rated by visually evaluating the degree of corn root damage by feeding larvae in conjunction with the physical presence of live and/or dead larvae. The results are tabulated in Table III.

EXAMPLE Q

Control of Mosquito Larvae

The compounds of the invention were tested for control of Mosquito larvae (*Aedis aegypti*). A plastic cup was first filled with 90 ml deionized water and then infested with early 4th-stage Mosquito larvae contained in 10 ml of water. One rabbit food pellet was added to the cup to provide food for the larvae. Twenty microliters of a 500-ppm solution of the toxicant were added to the cup. The water was then thoroughly mixed to give a 0.1-ppm solution of the toxicant. The test cup was covered with a plastic lid in order to prevent evaporation and to confine subsequent emerging adults. The test unit was held at 27° C. for 6 days. Mortality readings were then taken. The results for the test compounds are given in Table III.

TABLE I

Compounds of the Formula:

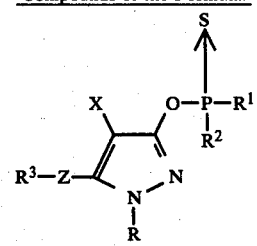

| | X | Z | R | R¹ | R² | R³ | Physical State | %C Calc. | %C Found | %H Calc. | %H Found | %N Calc. | %N Found |
|---|---|---|---|---|---|---|---|---|---|---|---|---|---|
| Compound No. | | | | | | | | | | | | | |
| 1 33759 | Cl | —SO₂— | CH₃ | OCH₂CH₃ | OCH₂CH₃ | CH₃ | Brown Oil | 32.59 | 30.41 | 4.86 | 4.63 | 8.44 | 7.76 |
| 2 40709 | Cl | —SO₂— | CH₃ | OCH₂CH₃ | OCH₂CH₃ | CH₂CH₃ | Yellow Oil | 33.30 | 32.60 | 5.03 | 4.98 | 7.77 | 5.89 |
| 3 39721 | Cl | —SO₂— | CH₃ | OCH₂CH₃ | CH₂CH₃ | CH₂CH₃ | Yellow Oil | 33.30 | 33.20 | 5.03 | 5.35 | 7.77 | 7.48 |
| Comparison Compound | | | | | | | | | | | | | |
| 4C | H | —S— | CH₃ | OCH₂CH₃ | OCH₂CH₃ | CH₂CH₃ | Light Yellow Oil | 38.70 | 38.71 | 6.18 | 6.16 | 9.03 | 9.13 |

TABLE II

| Compound No. | GDM | TLB | CLB | TEB | BR | BPM | RB |
|---|---|---|---|---|---|---|---|
| 1 | 0 | 0 | 23 | 54 | 0 | 93 | — |
| 2 | 0 | 0 | 14 | 0 | 0 | 0 | 0 |
| 3 | 50 | 4 | 25 | — | 19 | 86 | 77 |
| 4C | 19 | 0 | 0 | 36 | 0 | 0 | 0 |

GDM —Grape Downy Mildew (*Plasmopara viticola*)
TLB —Tomato Late Blight (*Phytophthora infestans conidia*)
CLB —Celery Late Blight (*Septoria apii*)
TEB —Tomato Early Blight (*Alternaria solani conidia*)
BR —Bean Rust Eradicant (*Uromydes phaseoli tipica*)
BPM —Bean Powdery Mildew (*Erysiphe polygoni*)
RB —Rice Blast (*Piricularia oryzae*)

TABLE III

| Compound No. | A. | A.S. | M. Ad. | M.E. | H. | A.C. | A.W. | R. | C.L. | M.Q. |
|---|---|---|---|---|---|---|---|---|---|---|
| | | | | INSECTICIDAL ACTIVITY % CONTROL | | | | | | |
| 1 | — | 0 | 99 | 99 | 85 | 100 | 100 | — | 80 | 100 |
| 2 | 100 | 0 | 35 | 0 | 83 | 100 | 100 | 0 | 20[1] | 100 |
| 3 | 100 | 0 | 93 | 95 | 80 | 100 | 100 | — | 100 | 100 |
| 4C | 100 | 0 | 98 | 60 | 65 | 100 | 100 | — | 0 | 100 |

A. —Aphids (*Aphis gossypii* Glover)
A.S. —Aphids Systemically (*Aphis gossypii* Glover)
M. Ad. —Mite Adult (*Tetranychus urticae*)
M.E. —Mite Egg Control (*Tetranychus urticae*)
H. —Housefly (*Musca domestica* L.)
A.C. —American Cockroach (*Periplaneta americana* L.)
A.W. —Alfalfa Weevil (*H. brunneispennis* Boheman)
R. —Rootworm (*Diabrotica undecimpunctata* u.)
C.L. —Cabbage Looper (*Trichoplusia ni*)
M.Q. —Mosquito Larvae (*Aedis aegypti*)
[1]80% @ 5 days.

What is claimed is:

1. A compound of the formula:

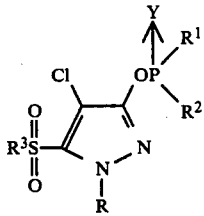

wherein R is lower alkyl; $R^1$ is lower alkoxy or lower alkylthio; $R^2$ is lower alkyl or lower alkoxy; $R^3$ is lower alkyl; and Y is sulfur or oxygen.

2. A compound of the formula defined in claim 1 wherein $R^1$ is lower alkoxy.

3. A compound of the formula defined in claim 2 wherein $R^2$ is lower alkoxy.

4. A compound of the formula defined in claim 2 wherein $R^2$ is lower alkyl.

5. A compound of the formula defined in claim 1 wherein Y is sulfur.

6. A compound of the formula defined in claim 5 wherein R is methyl.

7. A compound of the formula defined in claim 6 wherein $R^1$ is ethoxy, $R^2$ is ethoxy or ethyl, and $R^3$ is methyl or ethyl.

8. A compound of the formula defined in claim 7 wherein $R^2$ is ethoxy and $R^3$ is methyl.

9. A compound of the formula defined in claim 7 wherein $R^2$ is ethyl and $R^3$ is ethyl.

10. A method for controlling fungi which comprises applying to the fungus or its habitat a fungicidally effective amount of the compound of the formula defined in claim 1.

11. A method for controlling fungi which comprises applying to the fungus or its habitat a fungicidally effective amount of the compound of the formula defined in claim 3.

12. A method for controlling fungi which comprises applying to the fungus or its habitat a fungicidally effective amount of the compound of the formula defined in claim 4.

13. A method for controlling fungi which comprises applying to the fungus or its habitat a fungicidally effective amount of the compound of the formula defined in claim 7.

14. A method for controlling fungi which comprises applying to the fungus or its habitat a fungicidally effective amount of the compound of the formula defined in claim 8.

15. A method for controlling fungi which comprises applying to the fungus or its habitat a fungicidally effective amount of the compound of the formula defined in claim 9.

16. A method for killing insects which comprises contacting said insects or their habitat with an insecticidally effective amount of the compound of the formula defined in claim 1.

17. A method for killing insects which comprises contacting said insects or their habitat with an insecticidally effective amount of the compound of the formula defined in claim 3.

18. A method for killing insects which comprises contacting said insects or their habitat with an insecticidally effective amount of the compound of the formula defined in claim 4.

19. A method for killing insects which comprises contacting said insects or their habitat with an insecticidally effective amount of the compound of the formula defined in claim 7.

20. A method for killing insects which comprises contacting said insects or their habitat with an insecticidally effective amount of the compound of the formula defined in claim 8.

21. A method for killing insects which comprises contacting said insects or their habitat with an insecticidally effective amount of the compound of the formula defined in claim 9.

22. An insecticidal composition comprising a biologically inert carrier and a fungicidally effective amount of a compound of the formula defined in claim 1.

23. An insecticidal composition comprising a biologically inert carrier and a fungicidally effective amount of a compound of the formula defined in claim 3.

24. An insecticidal composition comprising a biologically inert carrier and a fungicidally effective amount of a compound of the formula defined in claim 4.

25. An insecticidal composition comprising a biologically inert carrier and a fungicidally effective amount of a compound of the formula defined in claim 7.

26. An insecticidal composition comprising a biologically inert carrier and a fungicidally effective amount of a compound of the formula defined in claim 8.

27. An insecticidal composition comprising a biologically inert carrier and a fungicidally effective amount of a compound of the formula defined in claim 9.

* * * * *